US009208772B2

(12) United States Patent
Yamkovoy

(10) Patent No.: US 9,208,772 B2
(45) Date of Patent: Dec. 8, 2015

(54) COMMUNICATIONS HEADSET SPEECH-BASED GAIN CONTROL

(75) Inventor: Paul G. Yamkovoy, Acton, MA (US)

(73) Assignee: BOSE CORPORATION, Framingham, MA (US)

( * ) Notice: Subject to any disclaimer, the term of this patent is extended or adjusted under 35 U.S.C. 154(b) by 940 days.

(21) Appl. No.: 13/336,207

(22) Filed: Dec. 23, 2011

(65) Prior Publication Data

US 2013/0163775 A1 Jun. 27, 2013

(51) Int. Cl.

| | |
|---|---|
| ***H03B 29/00*** | (2006.01) |
| ***G10K 11/16*** | (2006.01) |
| ***A61F 11/06*** | (2006.01) |
| ***G10K 11/178*** | (2006.01) |
| ***H04R 1/10*** | (2006.01) |
| *H04R 5/033* | (2006.01) |

(52) U.S. Cl.

CPC .......... *G10K 11/1782* (2013.01); *H04R 1/1083* (2013.01); *H04R 5/033* (2013.01); *H04R 2201/107* (2013.01); *H04R 2460/01* (2013.01)

(58) Field of Classification Search

CPC ...... H04R 1/10; H04R 3/005; H04R 2410/05; H04R 3/00; H04R 1/1083; H04R 2460/01; H04R 2201/107; H04R 5/033; G10K 11/16; G10K 11/1782; H03G 3/20

USPC ............... 381/71.6, 71.1, 375, 122, 150, 120, 381/71.8, 71.14; 704/233, 231

See application file for complete search history.

(56) References Cited

U.S. PATENT DOCUMENTS

| | | | | |
|---|---|---|---|---|
| 4,953,217 | A | 8/1990 | Twiney et al. | |
| 5,259,033 | A | 11/1993 | Goodings et al. | |
| 5,680,467 | A | 10/1997 | Hansen | |
| 5,764,779 | A * | 6/1998 | Haranishi | 381/71.1 |
| 6,920,227 | B2 | 7/2005 | Chalupper et al. | |
| 6,941,161 | B1 * | 9/2005 | Bobisuthi et al. | 455/569.1 |
| 7,346,176 | B1 * | 3/2008 | Bernardi et al. | 381/92 |
| 7,457,644 | B1 * | 11/2008 | Bobisuthi et al. | 455/570 |
| 7,561,700 | B1 * | 7/2009 | Bernardi et al. | 381/92 |
| 8,204,253 | B1 * | 6/2012 | Solbach | 381/94.7 |
| 8,208,650 | B2 | 6/2012 | Joho et al. | |
| 8,355,511 | B2 * | 1/2013 | Klein | 381/66 |
| 8,587,376 | B2 * | 11/2013 | Reining | 330/136 |
| 8,774,423 | B1 * | 7/2014 | Solbach | 381/94.1 |
| 8,781,147 | B1 * | 7/2014 | Giuroiu | 381/384 |
| 2004/0196984 | A1 * | 10/2004 | Dame et al. | 381/71.1 |
| 2005/0141730 | A1 * | 6/2005 | Murphy | 381/74 |

(Continued)

FOREIGN PATENT DOCUMENTS

| | | | |
|---|---|---|---|
| EP | 1608202 | A2 | 12/2005 |
| GB | 2246688 | A | 2/1992 |

(Continued)

OTHER PUBLICATIONS

International Search Report and Written Opinion dated Mar. 28, 2013 for International application No. PCT/ US2012/065865.

(Continued)

*Primary Examiner* — Vivian Chin
*Assistant Examiner* — Con P Tran

(57) ABSTRACT

A gain of a signal representing sounds detected by a talk-through and/or feedforward ANR microphone of a talk-through function provided by a communications headset is reduced in response to a user of the communications headset speaking.

9 Claims, 5 Drawing Sheets

(56) References Cited

U.S. PATENT DOCUMENTS

| | | | | |
|---|---|---|---|---|
| 2005/0276421 | A1* | 12/2005 | Bergeron et al. | 381/71.6 |
| 2006/0140416 | A1 | 6/2006 | Berg | |
| 2006/0262938 | A1* | 11/2006 | Gauger et al. | 381/56 |
| 2008/0004872 | A1* | 1/2008 | Nordholm et al. | 704/226 |
| 2009/0268933 | A1* | 10/2009 | Baechler | 381/318 |
| 2010/0172532 | A1* | 7/2010 | Gelhard et al. | 381/375 |
| 2010/0246807 | A1* | 9/2010 | Kemmochi et al. | 379/441 |
| 2010/0272279 | A1 | 10/2010 | Joho et al. | |
| 2010/0272280 | A1* | 10/2010 | Joho et al. | 381/71.6 |
| 2010/0278355 | A1 | 11/2010 | Yamkovoy | |
| 2011/0058696 | A1* | 3/2011 | Armstrong | 381/309 |
| 2011/0235813 | A1* | 9/2011 | Gauger, Jr. | 381/57 |
| 2011/0293102 | A1* | 12/2011 | Kitazawa et al. | 381/56 |
| 2012/0063611 | A1* | 3/2012 | Kimura | 381/71.6 |
| 2012/0106753 | A1* | 5/2012 | Theverapperuma et al. | 381/92 |

FOREIGN PATENT DOCUMENTS

| | | | |
|---|---|---|---|
| WO | 9908638 | A1 | 2/1999 |
| WO | 2010129219 | A1 | 11/2010 |
| WO | 2010129241 | A1 | 11/2010 |

OTHER PUBLICATIONS

International Search Report and Written Opinion dated Jun. 5, 2013 for International application No. PCT/ US2013/027786.

* cited by examiner

COMMUNICATIONS HEADSET SPEECH-BASED GAIN CONTROL

TECHNICAL FIELD

This disclosure relates to employing occurrences of speech detected by a communications microphone of a headset to control gain levels of one or both of ANR and TT audio.

BACKGROUND

With the advent of ever more effective forms of noise reduction in a communications headset to reduce the environmental noise sounds that reach the ears of its user, and possibly impede the user's ability to use the communications headset in two-way voice communications, a growing need has been identified to in some way allow speech sounds of another person in the vicinity of the user to still reach the ears of the user so as to allow the user to carry on a conversation with that other person without removing at least a portion of it from at least one of the user's ears. This has led to the introduction of a "talk-through" (TT) functionality being added to such a communications headset that employs one or more filtering techniques to separate speech sounds of such another person from other environmental sounds, and to pass those speech sounds through whatever passive noise reduction (PNR) or active noise reduction (ANR) functionality is provided by such a communications headset, and onward to an ear of its user. Unfortunately, difficulties persist in the provision of both ANR and TT functionality arising from infiltration and/or false triggering of audio compressors arising from a user's own speech.

An additional difficulty in some communications headsets to which ANR, TT and/or other functionality has been added is the accompanying need for increasingly complex signaling between separately encased components of those headsets that are often coupled by cabling. As those familiar with communications headsets meant to be coupled to an intercom system (ICS) or radio (e.g., an ICS or radio built into an aircraft or a military vehicle) will readily recognize, the preferred physical configuration frequently includes a control box that is physically separate and distinct from the earpieces and microphone making up a head assembly worn on a user's head. The provision of a control box is often intended to put manually-operable controls more easily in reach of a headset's user, as well as to lighten the head assembly by moving heavier components (e.g., batteries) into a portion of the headset that is not worn on its user's head. In such communications headsets, the control box is coupled by a cable to the head assembly, and as more functionality is added, this cable is often required to include more conductors, adding to its weight and making it less flexible.

SUMMARY

A gain of a signal representing sounds detected by a talk-through and/or feedforward ANR microphone of a talk-through function provided by a communications headset is reduced in response to a user of the communications headset speaking.

In one aspect, a communications headset includes a first earpiece; a first talk-through microphone carried by structure of the communications headset and acoustically coupled to an environment external to the communications headset; an audio circuit coupled to the first acoustic driver and the first talk-through microphone, the audio circuit comprising a first talk-through circuit receiving a signal representing sounds detected by the first talk-through microphone and providing its output to the first acoustic driver; and a communications microphone positioned relative to the first casing of the earpiece towards the vicinity of a mouth of a user of the communications headset, wherein the communications microphone is noise-canceling microphone. The first earpiece includes a first casing, and a first acoustic driver disposed therein. A gain of the signal representing sounds detected by the first talk-through microphone is reduced by a component of the first talk-through circuit in response to an instance of speech by a user of the communications headset being detected by the communications microphone.

It may be that the first talk-through circuit further includes a first audio amplifier to drive the acoustic driver with the output of the first talk-through circuit; a first envelope detector coupled to the output of the first audio amplifier to integrate peaks in a signal output by the first audio amplifier in driving the acoustic driver; and a first controllable attenuator interposed between the first talk-through microphone and an input of the first audio amplifier. And, it may be that the first envelope detector and the first controllable attenuator cooperate to form a first closed-loop compressor to limit an amplitude of the signal output by the first audio amplifier in response to the signal output by the first audio amplifier exceeding a predetermined threshold.

It may be that the audio circuit further includes a first ANR circuit receiving a signal representing noise sounds detected in the environment external to the communications headset, deriving anti-noise sounds, and providing the anti-noise sounds to the first acoustic driver; and a gain of the signal representing noise sounds is reduced by a component of the first ANR circuit in response to an instance of speech by a user of the communications headset being detected by the communications microphone. The noise sounds are detected by the first talk-through microphone, or through a first ANR microphone coupled to the audio circuit.

It may be that the communications headset further includes a second earpiece (wherein the second earpiece includes a second casing; and a second acoustic driver disposed therein); and a second talk-through microphone carried by structure of the communications headset and acoustically coupled to an environment external to the communications headset. Further, it may be that the audio circuit is further coupled to the second acoustic driver and the second talk-through microphone; the audio circuit further comprises a second talk-through circuit receiving a signal representing sounds detected by the second talk-through microphone and providing its output to the second acoustic driver; and a gain of the signal representing sounds detected by the second talk-through microphone is reduced by a component of the second talk-through circuit in response to an instance of speech by a user of the communications headset being detected by the communications microphone.

In another aspect, a method of controlling sounds acoustically output by an acoustic driver of a communications headset to an ear of a user of the communications headset includes: reducing a gain of a signal representing sounds detected by a talk-through microphone of the communications headset in response to detecting speech sounds of a user of the communications headset detected by a noise-canceling communications microphone of the communications headset such that an amplitude of sounds detected by the talk-through microphone that are acoustically output by the acoustic driver is reduced.

The method may further include integrating peaks of a signal output by the communications microphone; and controlling the reducing of the gain with the results of the integrating of the peaks. It may be that an envelope detector coupled to the communications microphone is employed to perform the integrating of the peaks; and a component of a talk-through circuit to which the talk-through microphone and the acoustic driver are coupled is employed to reduce the gain of the signal representing sounds detected by the talk-through microphone in a manner in which the combination of the envelope detector and the component of the talk-through circuit form an open-loop compressor. It may also be that the component of the talk-through circuit is a voltage-controlled attenuator comprising a gain control input coupled to the envelope detector, or an audio amplifier comprising a gain control input coupled to the envelope detector.

DETAILED DESCRIPTION

What is disclosed and what is claimed herein is intended to be applicable to a wide variety of communications headsets, i.e., devices structured to be worn on or about a user's head in a manner in which at least one acoustic driver is positioned in the vicinity of an ear, and in which a microphone is positioned towards the user's mouth to enable two-way audio communications. It should be noted that although specific embodiments of communications headsets incorporating a pair of acoustic drivers (one for each of a user's ears) are presented with some degree of detail, such presentations of specific embodiments are intended to facilitate understanding through examples, and should not be taken as limiting either the scope of disclosure or the scope of claim coverage.

It is intended that what is disclosed and what is claimed herein is applicable to headsets that also provide active noise reduction (ANR), passive noise reduction (PNR), or a combination of both. It is intended that what is disclosed and what is claimed herein is applicable to headsets meant to be coupled to at least an intercom system (ICS) or radio through a wired connection, but which may be further structured to be connected to any number of additional devices through wired and/or wireless connections. It is intended that what is disclosed and what is claimed herein is applicable to headsets having physical configurations structured to be worn in the vicinity of either one or both ears of a user, including and not limited to, over-the-head headsets with either one or two earpieces, behind-the-neck headsets, two-piece headsets incorporating at least one earpiece and a physically separate microphone worn on or about the neck, as well as hats or helmets incorporating earpieces and microphone(s) to enable audio communication. Still other embodiments of headsets to which what is disclosed and what is claimed herein is applicable will be apparent to those skilled in the art.

Figure 1:
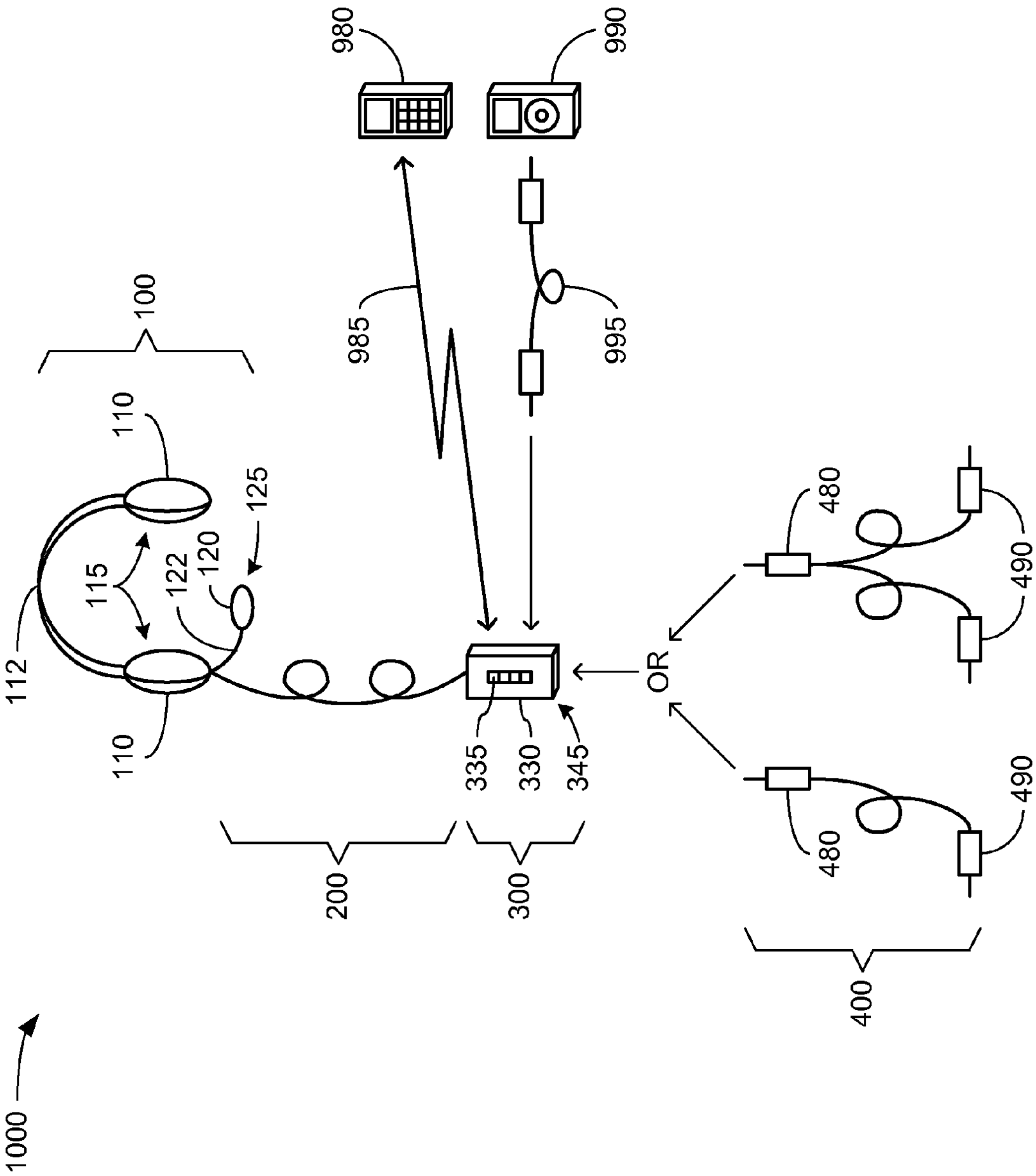
FIG. 1 is a perspective diagram of a communications headset.

FIG. 1 depicts an embodiment of a communications headset 1000 meant to be coupled to a communications device, such as an ICS or radio. The headset 1000 incorporates a head assembly 100, an upper cable 200, a control box 300, and a lower cable 400. The head assembly 100 incorporates a pair of earpieces 110 that each incorporate one of a pair of acoustic drivers 115, a headband 112 that couples together the earpieces 110, a microphone boom 122 extending from one of the earpieces 110, and a microphone casing 120 supported by the microphone boom 122 and incorporating a noise-canceling communications microphone 125. Further incorporated into the casing of at least one of the earpieces 110 and/or of another component of the head assembly 100 is an audio circuit 600 electrically coupled to the acoustic drivers 115 and/or the communications microphone 125. As depicted, the communications headset 1000 has an "over-the-head" physical configuration commonly found among communications headsets employed in airplanes, helicopters, military vehicles, etc. Depending on the size of each of the earpieces 110 relative to the typical size of the pinna of a human ear, each of the earpieces 110 may be either an "on-ear" (also commonly called "supra-aural") or an "around-ear" (also commonly called "circum-aural") form of earcup. However, despite the depiction in FIG. 1 of this particular physical configuration of the head assembly 100, those skilled in the art will readily recognize that the head assembly may take any of a variety of other physical configurations, including physical configurations having only one of the earpieces 110 (and correspondingly, only one of the acoustic drivers 115), physical configurations employing a napeband meant to extend between the earpieces 110 about the back of a user's neck, and/or physical configurations having no band at all.

The control box 300 incorporates a casing 330 that incorporates a control circuit 700. The control box 300 may also incorporate one or more manually-operable controls 335 enabling a user of the communications headset 1000 to manually control aspects of various functions performed by the communications headset 1000. The control box may further incorporate at least a compartment (not shown) for a battery 345 and/or the battery 345, itself, coupled to the control circuit 700.

The upper cable 200 is made up principally of a multiple-conductor electrical cable extending between and coupling one of the earpieces 110 of the head assembly 100 to the control box 300. In so doing, at least a subset of the conductors of the upper cable 200 couple and convey electrical signals (including electric power) between the audio circuit 600 of the head assembly 100 and the control circuit 700 of the control box 300. In various possible variants of the communications headset 1000, the upper cable 200 may be formed with a coiled shape as a convenience to users of the headset 1000. Also, in various possible variants of the communications headset 1000, the upper cable 200 may additionally incorporate one or more connectors (not shown) on the upper cable 200 where the upper cable 200 is coupled to one of the earpieces 110 and/or where the upper cable 200 is coupled to the casing 330 of the control box 300, thereby making the upper cable 200 detachable from one or both of the head assembly 100 and the control box 300.

The lower cable 400 is made up principally of another multiple-conductor electrical cable extending from the control box 300, different variants of which end with one or more connectors 490 (two variants being depicted) that are meant to enable the communications headset 1000 to be detachably coupled to any of a variety of communications devices (e.g., an ICS and/or radio). In so doing, at least a subset of the conductors of the lower cable 400 couple and convey electrical signals (including electric power) between the control circuit 700 of the control box 300 and circuitry of whatever communications device to which the connector(s) 490 may be coupled. Not unlike the upper cable 200, in various possible variants, the lower cable 400 may be formed with a coiled shape as a convenience to users of the headset 1000. Also, in various possible variants of the communications headset 1000 the lower cable 400 may additionally incorporate one or more connectors 480 where the lower cable 400 is coupled to a connector (not shown) of the control box 300, thereby making the lower cable 400 detachable from the control box 300.

As also depicted in FIG. 1, various variations of the communications headset 1000 are capable of performing various other functions beyond simply enabling its user to engage in two-way voice communications through whatever communications device that the communications headset 1000 is coupled to via the lower cable 400. The headset 1000 may incorporate a wireless transceiver enabling it to be coupled via wireless signals 985 (e.g., infrared signals, radio frequency signals, etc.) to a wireless device 980 (e.g., a cellphone, an audio playback/recording device, a two-way radio, etc.) to thereby enable a user of the headset 1000 to additionally interact with the wireless device 980 through the headset 1000. Alternatively or additionally, the headset 1000 may incorporate an auxiliary interface (e.g., some form of connector to at least receive analog or digital signals representing audio) enabling the headset 1000 to be coupled through some form of optically or electrically conductive cabling 995 to a wired device 990 (e.g., an audio playback device, an entertainment radio, etc.) to enable a user to at least listen through the headset 1000 to audio provided by the wired device 990. Where the control box 300 incorporates the manually-operable controls 335, the manually-operable controls 335 may enable a user of the headset 1000 to coordinate the transfer of audio among the headset 1000, the wireless device 980, the wired device 990, and whatever communications device to which the headset 1000 may be coupled via the lower cable 400.

Figure 2:
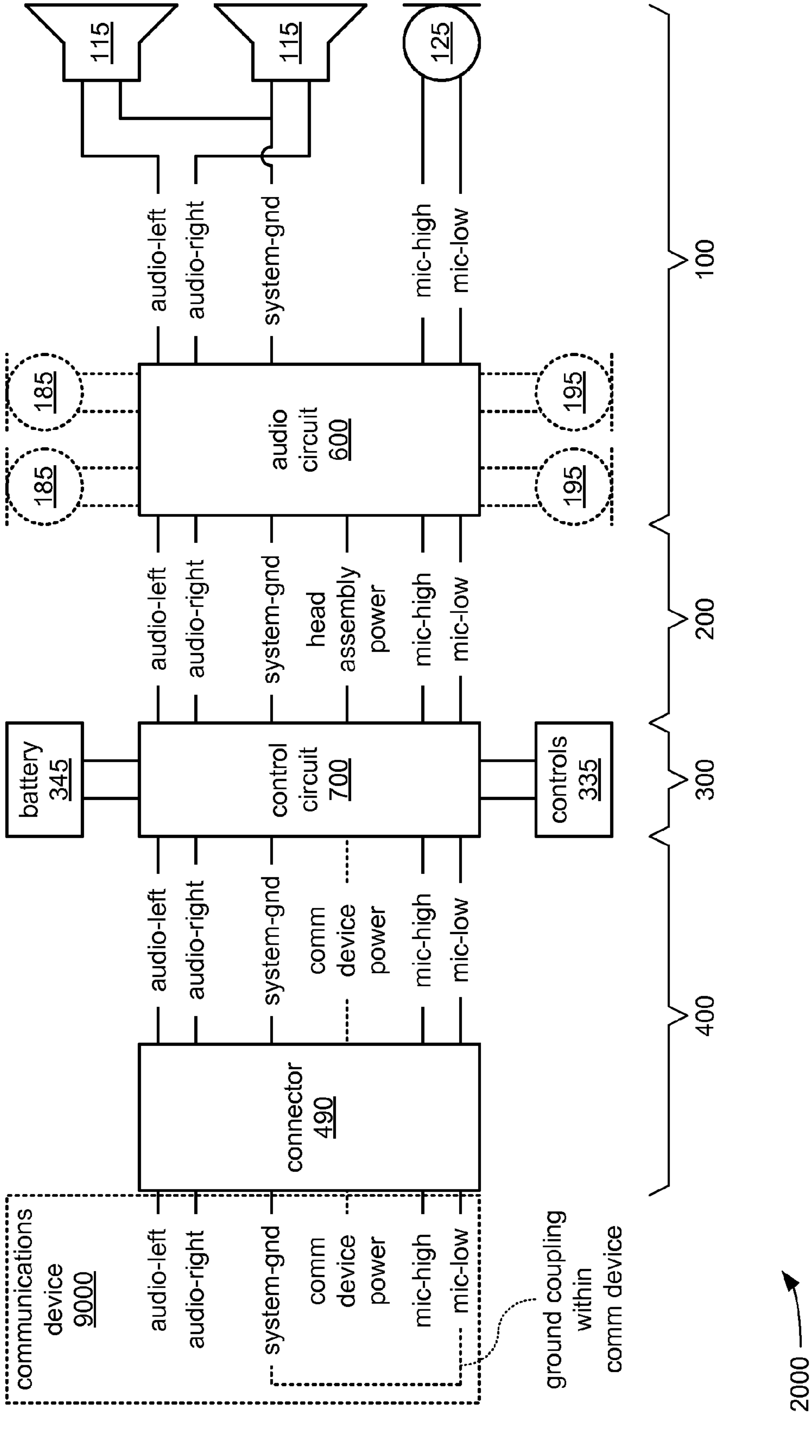
FIG. 2 is a block diagram of a possible electrical architecture of the communications headset of FIG. 1.

FIG. 2 depicts a possible embodiment of an electrical architecture 2000 that may be employed by the communications headset 1000. To facilitate understanding, the headset 1000 is depicted as being coupled to a communications device 9000 (e.g., an ICS or radio) with only portions of the communications device 9000 needed to facilitate discussion being depicted (in broken lines) for sake of visual clarity. Mirroring what was depicted in FIG. 1, FIG. 2 depicts the coupling of the head assembly 100 to the control box 300 via the upper cable 200, and depicts the coupling of the control box 300 to the communications device 9000 via the lower cable 400. However, FIG. 2 further depicts individual conductors of each of the cables 200 and 400.

It should again be noted that the audio circuit 600 may be carried entirely within the casing of only one of the earpieces 110; or may be divided into multiple portions, possibly with a portion within the casings of each of the earpieces 110 (in variants of the headset 1000 having a pair of the earpieces 110), and/or with a portion within the casing 120 that carries the communications microphone 125, and/or within one or more portions distributed elsewhere in the structure of the communications headset 1000. Thus, although FIG. 2 and subsequent figures depict the audio circuit 600 with a single block for ease of discussion, this should not be taken as an indication that the entirety of the audio circuit 600 necessarily exists within a single location of the structure of the headset 1000.

As depicted, in the electrical architecture 2000, audio-left and audio-right signals, along with an accompanying common system-gnd serving as a signal return, extend between the communications device 9000 and corresponding ones of the acoustic drivers 115 through conductors within the head assembly 100, conductors of the cables 200 and 400, and portions of the circuits 600 and 700. The provision of the separate audio-left and audio-right signals enables the provision of stereo audio to the ears of a user of the headset 1000. As also depicted, mic-high and mic-low signals extend between the communications device 9000 and the communications microphone 125 also through conductors within the head assembly 100, conductors of the cables 200 and 400, and portions of the circuits 600 and 700.

As will be familiar to those skilled in the art, widespread industry practice and/or government regulations in specific industries often dictate that specific forms of communications device (e.g., a radio built into an airplane or armored military vehicle) provide a microphone bias voltage across the conductors associated with coupling a headset microphone to those forms of communications device to accommodate some types of microphones requiring a bias voltage. As will be familiar to those skilled in the art, it is considered a best practice to maintain the conductors coupling a headset microphone to an ICS or radio (e.g., the conductors mic-low and mic-high depicted in FIG. 2) as entirely separate from the conductors coupling a headset acoustic driver to an ICS or radio (e.g., the conductors audio-left, audio-right and system-gnd depicted in FIG. 2). As part of such best practice, any coupling of any ground conductors among the conductors associated with that microphone and those associated with that acoustic driver occurs only within the ICS or radio (as depicted with a dotted line) in an effort to avoid the creation of a ground loop extending along the length of whatever cabling couples a headset to an ICS or radio.

Further, and with somewhat less consistency even within a given industry, various forms of communications device may or may not provide a communications headset with electric power via still another conductor coupling that communications device to that headset (e.g., a communications device power conductor, as depicted). Where such power is so provided, it is usually referenced to whatever ground conductor is associated with an acoustic driver of that headset, and not one of the conductors associated with a microphone of that headset. As previously depicted and discussed, the lower cable 400 may be detachable from the control box 300 to allow different versions of the lower cable 400 having different versions of the connector(s) 490 to be used in order to accommodate different forms of a communications device. As will be familiar to those skilled in the art, the different versions of mating connectors with which the communications device 9000 may be provided may or may not support the provision of electric power to a headset, and thus, this is among the differences that may be accommodated with different versions of the lower cable 400.

Thus, as depicted, the control circuit 700 is provided with power from one or both of communications device 9000 (via the communications device power conductor of the lower cable 400) and the battery 345. In keeping with other best practices, a ground conductor of the battery 345 is typically coupled to the common system-gnd. In turn, at least one head assembly power conductor of the upper cable 200 then conveys power provided to the control circuit 700 from whatever source to the audio circuit 600. As will shortly be explained in greater detail, the communications headset 1000 may use electric power in performing various functions including, and not limited to, amplifying audio for acoustic output by the acoustic drivers 115, pre-amplifying audio detected by the communications microphone 125, providing one or more forms of ANR (hence the depiction of the possible coupling of ANR microphones 195 to the audio circuit 600 in dotted lines), powering a wireless transceiver to send and/or receive audio (e.g., whatever wireless transceiver may be used to form the communications link 985), performing any of a variety of forms of signal processing on audio acoustically output by the acoustic drivers 115 and/or detected by the communications microphone 125, and/or providing a talk-through (TT) function to enable selective passage of speech sounds from the environment external to the casings 110 through whatever passive noise reduction (PNR) and/or ANR that may be provided by the communications headset 1000 so as to reach the ears of a user (hence the depiction of the possible coupling of talk-through microphone 185 to the audio circuit 600 in dotted lines).

As will be familiar to those skilled in the art will readily recognize, government regulations often require that a degree of "failsafe" design be employed in communications headsets such that the basic functionality of carrying out two-way communications (i.e., using a communications headset with whatever ICS or radio it may be coupled to) not be lost as a result of a loss of power to the communications headset. Thus, the acoustic drivers 115 and the communications microphone 125 must still be operational even if no power is provided by the communications device 9000, by the battery 345, or by any other source. For this reason, it is common practice to provide a mechanism by which signals employed in such basic operation of the acoustic drivers 115 and the communications microphone 125 will be made to bypass any amplification or other circuitry (i.e., be conducted among the connector(s) 490, the acoustic drivers 115 and communications microphone 125 without interruption) when such power loss occurs.

As will also be explained in greater detail, electric power may be conveyed by at least one head assembly power conductor of the upper cable 400 to the audio circuit 600 with a selectively variable voltage level as a mechanism to control one or more aspects of the performance of one or more of these various functions. In this way control signals may be conveyed from the control circuit 700 to the audio circuit 600 without use of distinct control conductors added to the upper cable 400 and without use of a digital serial signaling system that could add undesirably complex encoder and decoder circuitry to the control circuit 700 and the audio circuit 600. What the audio circuit 600 is signaled to do in performing one or more functions may be determined by a user through their operation of the manually-operable controls 335 and/or may be determined in a more automated manner in response to available electric power. Avoiding the addition of distinct control signal conductors and digital serial signaling reduces avenues for the introduction of electromagnetic interference (EMI) as a result of reducing the quantity of conductors that may tend to act as antennae for receiving EMI, as a result of having numerous transitions in voltage level and/or direction in current flow due to convey digital serial signals, and as a result of employing power conductors (which tend to act as an AC-coupled short to ground) as signal conductors.

Figure 3:
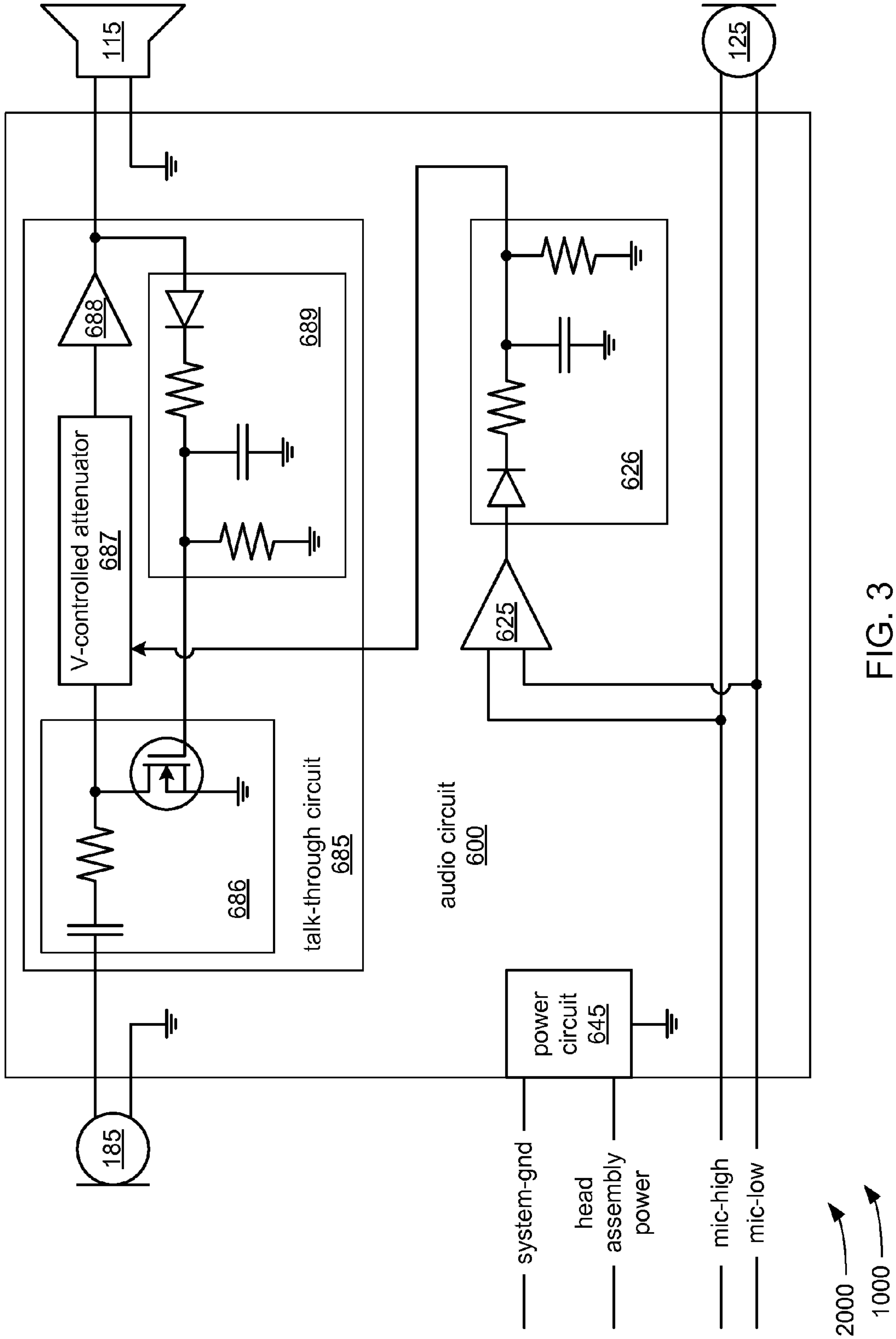
FIG. 3 is a block diagram of portions of one variant of the electrical architecture of FIG. 2 incorporating a variable talk-through gain.

FIG. 3 depicts portions of one possible variant of the electrical architecture 2000 introduced in FIG. 2 germane to implementing automated variation in gain in the provision of talk-through functionality. Thus, portions more germane to other features of the architecture 2000 of the communications headset 1000 have been omitted for sake of clarity. Also for sake of clarity, components of the audio circuit 600 associated with one of the earpieces 110 are depicted. Thus, although what is depicted in FIG. 3 may be part of a form of the communications headset 1000 that incorporates a pair of earpieces 110 (and therefore, at least a pair of the acoustic drivers 115, as well as duplicate sets of associated components within the audio circuit 600), only one of the acoustic drivers 115 and its associated components within the audio circuit 600 are depicted to avoid unnecessary visual clutter in FIG. 3.

As depicted, the audio circuit 600 in this variant of the electrical architecture 2000 incorporates a talk-through circuit 685 coupled to the acoustic driver 115 and the talk-through microphone 185 to provide talk-through functionality, a differential amplifier 625 to tap electrical signals representing audio detected by the communications microphone 125, and an envelope detector 626 coupled to both the output of the differential amplifier 625 and to the talk-through circuit 685 associated with the one acoustic driver 115. The audio circuit 600 is also depicted as incorporating a power circuit 645 coupled to head assembly power and system-gnd conductors of the upper cable 400 to receive electrical power from the control circuit 700, and coupled to various other components of at least the audio circuit 600 to distribute the received electrical power to those other components (though for sake of visual clarity, a subset of only the ground couplings is actually depicted). In turn, the talk-through circuit 685 is depicted as incorporating a controllable attenuator 686 coupled to the talk-through microphone 185, a voltage-controlled attenuator 687 coupled to the output of the controllable attenuator 686, an audio amplifier 688 coupled by its input to the output of the voltage-controlled attenuator 687 and by its output to the acoustic driver 115, and an envelope detector 689 also coupled to the output of the audio amplifier 688 and coupled to a control input of the controllable attenuator 686.

Again, it should be noted that only a single acoustic driver 115 and its associated circuitry within the audio circuit 600 (e.g., the talk-through circuit 685) are depicted for sake of visual clarity. Thus, in embodiments of the communications headset 1000 having a pair of the earpieces 110, there would be a pair of the acoustic drivers 115, each having an associated one of a pair of the talk-through circuits 685 coupled to it, and the single envelope detector 626 would be coupled to each of those talk-through circuits 685.

It should be noted that unlike the communications microphone 125, the talk-through microphone 185 is not a noise-canceling microphone, and this reflects differences in the functions performed by each. It is advantageous and preferred that the communications microphone 125 be a noise-canceling type of microphone such that it is a near-field microphone that detects almost exclusively the speech sounds emanating from the mouth of a user of the communications headset 1000 (while tending to ignore far-field sounds). In contrast, it is advantageous and preferred that the talk-through microphone 185 not be such a noise-canceling type of microphone such that it is able to function to detect far-field sounds (e.g., the speech sounds emanating from someone other than the user), as well as near field.

As those familiar with talk-through functionality will readily recognize, the talk-through circuit 685 operates to convey speech sounds emanating from persons other than a user of the communications headset 1000, as detected by the talk-through microphone 185 (carried by a portion of the communications headset 1000 in such a manner as to acoustically couple it to the external environment), to the acoustic driver 115 to allow the user to hear those speech sounds despite whatever PNR and/or ANR is provided by the communications headset 1000, which would otherwise normally prevent those speech sounds from being heard by the user. To avoid conveying sounds other than speech sounds through such PNR and/or ANR, the talk-through circuit 685 conveys only sounds detected by the talk-through microphone 185 that are within a predetermined range of audio frequencies associated with human speech. Although variants of the talk-through circuit 685 are possible that incorporate a distinct bandpass filter (not shown) that would separate sounds within such a range to be conveyed from sounds outside such a range to not be conveyed, variants of the talk-through circuit 685 are possible that employ a band-limited variant of the audio amplifier 688 such that the audio amplifier 688 performs this bandpass filtering function in addition to amplification.

The envelope detector 689 and the controllable attenuator 686 cooperate to form one possible implementation of an audio compressor that monitors the amplitude of the output of the audio amplifier 688, and that acts to variably reduce the amplitude of the audio signal received by from the talk-through microphone 185 in response to detecting instances of the amplitude of the output of the audio amplifier 688 provided to the acoustic driver 115 exceeding a predetermined threshold. Thus, this compressor created through this cooperation is a closed-loop compressor. It should be noted that alternate implementations of the talk-through circuit 685 are possible in which this audio compressor is not present and with the input of the audio amplifier 688 being more directly coupled to the talk-through microphone 185 (i.e., perhaps with only the voltage-controlled attenuator 687 between them). However, it is seen as desirable to provide such audio compression functionality, however implemented, in the talk-through circuit 685 as a safety feature to protect the hearing of a user of the communications headset 1000 by preventing excessively loud environmental sounds from being conveyed by the talk-through circuit 685 to an ear of the user.

The controllable attenuator 686 is formed from a combination of a capacitor, a resistor and a MOSFET coupled in a manner providing both AC coupling to the talk-through microphone 185 and a variable voltage divider that will be readily familiar to those skilled in the art of audio compression. The gate input of the MOSFET is coupled to the envelope detector 689, and it is via this gate input that control of the degree of attenuation of the audio received at the input of the audio amplifier 688 from the talk-through microphone 185 is effected.

The envelope detector 689 is formed from a combination of a diode, resistors and a capacitor coupled in a manner that will also be readily familiar to those skilled in the art of audio compression. The anode of the diode is coupled to the output of the audio amplifier 688, and its cathode is coupled to a first one of the resistors. In turn, the first one of the resistors is further coupled to the capacitor and the second one of the resistors (both of which are further coupled to ground), as well as to the gate input of the MOSFET of the controllable attenuator 686. The diode enables current to flow from the output of the audio amplifier 688 in a manner that charges the capacitor through the first resistor (with the first resistor controlling the rate of charging), but does not allow that charge to be subsequently drained by the output of the audio amplifier 688. Instead, it is the second resistor that provides a controlled rate of drain of that charge—the gate input of the MOSFET of the controllable attenuator 686 having too high an impedance to ground to provide another path of current flow by which the capacitor may be drained. Thus, the envelope detector, effectively acts as an integrator of peaks in the audio signal output by the audio amplifier 688, with the capacitor storing a charge built up by the higher amplitudes of the output of that signal, and discharging at a controlled rate through the second resistor, with the resulting voltage level to which the capacitor has been charged being presented to the gate input of the MOSFET.

It should be noted that the depiction of the envelope detector 689 in FIG. 3 may be more symbolic of its theory of operation than schematic, as various component substitutions may be made as those skilled in the art will readily recognize. For example, the depicted passive diode may be replaced with an active circuit having a behavior that more closely befits an ideal diode in which the forward bias voltage drop is (or is quite close to) zero. It should also be noted that since the diode and the first resistor are coupled in series to convey the output of the audio amplifier 688 therethrough, the order in which they are depicted as being coupled in FIG. 3 may be reversed. It should further be noted that, as depicted, the envelope detector 689 is a variant of half-wave envelope detector that detects peaks, and that as an alternative, full-wave variants are possible that detect both peaks and troughs. In other words, to put it more broadly, the envelope detector 689 may be implemented in any of a variety of ways other than what is depicted in FIG. 3.

By interposing the envelope detector 689 between the output of the audio amplifier 688 and the gate input of the MOSFET of the controllable attenuator 686 (as opposed to more directly coupling the output of the audio amplifier 688 to that gate input), the controllable attenuator 686 is prevented from being caused to provide and cease to provide attenuation of the signal from the talk-through microphone with each peak that occurs in the output of the audio amplifier 688. Instead, the controllable attenuator 686 is caused to provide attenuation in a more continuous manner throughout periods of time in which multiple peaks exceeding the predetermined threshold for the output of the audio amplifier 688 occur, and to cease providing attenuation only after such periods have passed. In causing the controllable attenuator 686 to behave in this manner, the time delay by which the envelope detector 689 responds to the occurrence of a peak (either an isolated peak or the first of multiple adjacent peaks) exceeding the predetermined threshold (also known as the "attack time") is necessarily set by resistance of the first resistor and the capacitance of the capacitor, as those skilled in RC circuits will readily recognize. Further, the time required for the capacitor to drain sufficiently that the MOSFET is no long provided with a voltage triggering attenuation (also known as the "decay time") is necessarily set by the capacitance of the capacitor and the resistance of the second resistor. Thus, the choice of the capacitance of the capacitor and the resistances of the first and second resistors determine the behavior of the compressor function brought about by the cooperation of the envelope detector 689 and the controllable attenuator 686.

The envelope detector 626 is formed from a combination of a diode, resistors and a capacitor coupled in a manner that is substantially similar to what has just been described of the envelope detector 689 (but, just as in the case of the envelope detector 689, the envelope detector 626 may be implemented in any of a variety ways. However, instead of being employed to integrate peaks in the signal output by the audio amplifier 688, the envelope detector 626 is employed to integrate peaks in the signal output by the communications microphone 125, as received by the envelope detector 626 through the differential amplifier 625. As previously discussed, it is considered a best practice to effect any coupling of one of the mic-low or mic-high conductors to ground only at the location of whatever communications device to which the communications headset 1000 is coupled through the connector(s) 490 (e.g., the communications device 9000). Thus, coupling the positive and negative inputs of the differential amplifier 625 to the mic-low and mic-high conductors enables whatever signal carried by them to be tapped without causing either of them to be coupled to ground at the location of the audio circuit 600

(taking advantage of the very high impedance of typical differential amplifiers). Still, as those skilled in the art will readily recognize, it is not inconceivable to use a single-ended variant of amplifier in place of the differential amplifier 625, perhaps along with coupling the mic-low signal to ground within the audio circuit 600 while coupling the mic-high signal to the single-ended input of such an amplifier.

The output of the integration performed by the envelope detector 626 is coupled to a gain input of the voltage-controlled attenuator 687, thereby allowing a signal representing an integration of peaks in signals representing audio detected by the communications microphone 125 to be employed to selectively reduce the gain of the signal representing sounds detected by the talk-through microphone 185 that is provided to the input of the audio amplifier 688. It should be noted that although FIG. 3 depicts the use of an attenuator that is a separate and distinct component from the audio amplifier 688 to serve as the mechanism by which gain may be reduced under the control of the envelope detector 626, other embodiments are possible in which the gain of the audio amplifier 688 is controllable and the envelope detector 626 is more directly coupled to the audio amplifier 688 (i.e., coupled in some manner to a gain control input of the audio amplifier 688) to employ the audio amplifier 688 as the mechanism by which gain may be so reduced. This depiction of a separate and distinct component to actually effect a reduction in gain has been done partially to make clear that it is a reduction in gain that is meant to be carried out under the control of the envelope detector 626, and not an increase.

In this way, a linkage between differential signal activity occurring across the mic-low and mic-high conductors and a reduction of the gain of talk-through audio is formed such that when a user of the communications headset 1000 speaks, the gain of the signal representing sounds detected by the talk-through microphone 185 is reduced for a period of time that starts with an attack time and ends with a decay time that are at least partially controlled by the capacitance of the capacitor and the resistances of the resistors of the envelope detector 626. Thus, an open-loop compressor is formed by the interaction between the envelope detector 626 and the voltage-controlled attenuator 687 to implement this linkage. This addresses the problem of a user of the communications headset 1000 hearing his own voice to a greater than normal degree through the talk-through functionality of the communications headset 1000 whenever the user speaks. As those familiar with the physiology and acoustics of human speech will readily recognize, it is normal for a person to hear their own speech sounds when they speak, partially as a result of vocal sounds being internally conveyed to their ears through the Eustachian tubes, bone conduction and conduction through other structures within the neck and head; and partially as a result of vocal sounds being carried in the air from the vicinity of their mouth to the vicinities of both of their ears (presuming that the entrances to their ear canals are not covered). However, although hearing themselves talk to such a degree is normal, it is very possible that the talk-through functionality of the communications headset 1000 may cause a user's own voice to be conveyed to their ears with an unnaturally high amplitude and/or altered in some other way that may be unpleasant and/or distracting, and which may mask other sounds that they desire to hear.

Further, depending on the placement of the talk-through microphone 185 relative to the vicinity of a user's mouth and/or how loudly they speak, it is possible that their own speech sounds may be detected by the talk-through microphone 185 as being sufficiently loud that amplification at a normal gain level by the audio amplifier 688 causes triggering of the compression function provided by the combination of the envelope detector 689 and the controllable attenuator 686. Thus, instead of a user hearing their own voice to a degree that is unnaturally loud and/or in a manner that is unnatural in other ways through the talk-through functionality, the user may experience a momentary loss of talk-through functionality that lasts both while they are speaking and for the duration of the decay time following the instant they cease speaking. Depending on the length of the decay time, this could actually impede a user having a conversation with someone else by causing the user to become unable to hear what the other person is saying whenever the user speaks and for some additional period of time (i.e., the decay time) after the user stops talking. In effect, for example, a user of the communications headset 1000 may ask someone else a question, but be unable to hear at least the start of the other person's answer to that question. By reducing the gain with which the signal representing sounds detected by the talk-through microphone 185 is provided to the audio amplifier 688 whenever the user speaks, talk-through functionality is maintained, but at a reduced gain level that both prevents the user from hearing their own voice at an unnaturally loud level and that also precludes the output of the audio amplifier 688 reaching an amplitude that triggers compression.

In order for the addition of the open-loop compressor formed by the combination of the envelope detector 626 and the voltage-controlled attenuator 687 to effectively prevent unwanted triggering of the closed-loop compressor formed by the combination of the envelope detector 689 and the controllable attenuator 686, at least the attack time of the open-loop compressor formed by the combination of the envelop detector 626 and the voltage-controlled attenuator 687 must be shorter than the attack time of the closed-loop compressor formed by the combination of the envelop detector 689 and the controllable attenuator 686. However, it is preferred that this open-loop compressor operate generally faster than this closed-loop compressor, and therefore, it is preferable that the decay time of this open-loop compressor is also shorter than the decay time of this closed-loop compressor.

Figure 4:
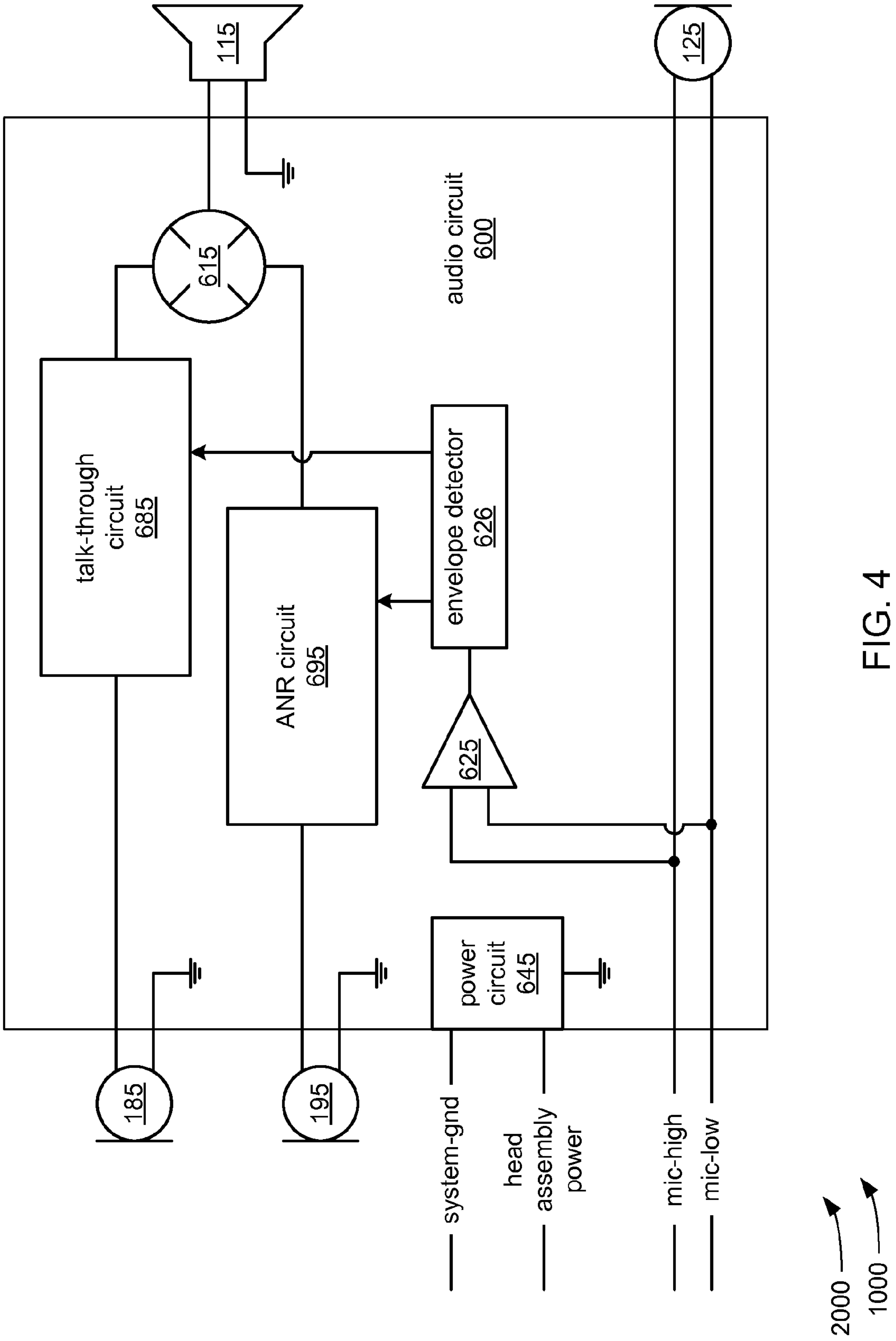
FIG. 4 is a block diagram of portions of another variant of the electrical architecture of FIG. 2 incorporating a variable ANR and talk-through gains.

FIG. 4 depicts portions of another possible variant of the electrical architecture 2000 introduced in FIG. 2 germane to implementing automated reduction in gain in the provision of talk-through functionality. Again, for sake of clarity, components of the audio circuit 600 associated with only one of the earpieces 110 (and therefore, only one of the acoustic drivers 115) are depicted. This variant differs from the variant depicted in FIG. 3 only to the extent that a gain employed in the provision of ANR is now also reduced in response to the detection of a user's speech in addition to reducing the gain employed in the provision of talk-through functionality (as just discussed at length with regard to FIG. 3). Given the extensive treatment of numerous implementation details just provided with regard to FIG. 3, it was deemed unnecessary to repeat such an extensive depiction of detail, and therefore, FIG. 4 presents a somewhat higher-level view of a mechanism employed to reduce gain(s) in response to instances of a user speaking.

As already discussed with regard to FIG. 3, the envelope detector 626 integrates peaks and in the differential audio signals present across the mic-low and mic-high conductors, and presents the result of this integration as a signal to a component of the talk-through circuit 685 to cause the gain of a signal representing talk-through sounds detected by the talk-through microphone 185 to be reduced in response to there being signal activity present on the mic-low and mic-high conductors (i.e., as a result of instances of a user speaking, as detected by the communications microphone 125). However, in the variant depicted in FIG. 4, another signal representing results of this integration is presented to the gain input of a corresponding component of an ANR circuit 695 coupled to at least one of the feedforward microphone 195 as part of providing feedforward-based ANR. Thus, in response to instances of the user speaking (as detected by the communications microphone 125), the gain of a signal representing feedforward noise sounds detected by the feedforward microphone 195 and employed in deriving feedforward anti-noise sounds is also reduced. The outputs of the audio amplifiers of both the talk-through circuit 685 and the ANR circuit 695 are coupled to and combined by a summing node 615, which in turn, is coupled to the acoustic driver 115 to drive the acoustic driver 115 with a signal resulting from that combination.

Again, it should be noted that only a single acoustic driver 115 and its associated circuitry within the audio circuit 600 (e.g., the talk-through circuit 685 and the ANR circuit 695) are depicted for sake of visual clarity. Thus, in embodiments of the communications headset 1000 having a pair of the earpieces 110, there would be a pair of the acoustic drivers 115, each having an associated one of a pair of the talk-through circuits 685 and an associated one of a pair of ANR circuits 695 coupled to it, and the single envelope detector 626 would be coupled to each of those talk-through circuits 685 and each one of those ANR circuits 695.

It should be noted that embodiments are possible in which a single audio amplifier is employed to drive the acoustic driver 115 with a signal formed from combining talk-through and feedforward-based ANR signals at a point preceding the input to the single audio amplifier. However, providing each of the talk-through circuit 685 and the ANR circuit 695 more easily enables whatever closed-loop compressors that may be implemented within either to remain separate, thereby enabling those closed-loop compressors to be separately triggered with different attack and decay times and/or other differing characteristics. Also, in alternate embodiments in which variable gain features of audio amplifiers are employed in reducing gains (instead of separate and distinct gain reduction components) in response to instances of a user speaking, it may be deemed desirable to provide the talk-through circuit 685 and the ANR circuit 695 with separate audio amplifiers, as this would enable each audio amplifier's gain to be reduced at a different rate and/or with a different curve, if needed.

As those familiar with ANR will readily recognize, both feedback-based and feedforward-based forms of ANR entail detecting unwanted noise sounds with one or more microphones, deriving anti-noise sounds and then acoustically outputting those anti-noise sounds at a location and with a timing selected to cause destructive acoustic interference with the unwanted noise sounds to at least reduce their acoustic amplitude. In embodiments in which the communications headset 1000 incorporates feedforward-based ANR, at least one of the feedforward microphone 195 is carried by a portion of the headset 1000 (preferably, the casing of one of the earpieces 110) such that it is acoustically coupled to the environment external to the acoustic volumes enclosed by the earpieces 110 in the vicinity of an ear in order to detect unwanted noise sounds in that external environment. In embodiments in which the communications headset 1000 incorporates feedback-based ANR, at least one feedback microphone (not shown) is carried within the acoustic volume enclosed by one of the earpieces 110 in the vicinity of an ear in order to detect unwanted noise sounds from that external environment that have entered into the enclosed acoustic volumes. With either form of ANR, the ANR circuit 695 receives electrical signals representing the unwanted noise sounds from one or more microphones, and employs those noise sounds as reference sounds from which to generate the anti-noise sounds, which are then provided to the amplifier 697 to drive the acoustic driver 115 to acoustically output the anti-noise sounds. As those skilled in the details of ANR will readily recognize, the coexistence of a microphone within an enclosed acoustic volume and the acoustic driver 115 creates a partially electrical and partially acoustic feedback loop—hence the term feedback-based ANR. In contrast, the acoustic coupling of a microphone to the external environment in support of creating anti-noise sounds for acoustic output by the acoustic driver 115 within the enclosed acoustic volume does not form a feedback loop.

Returning more specifically to what is depicted in FIG. 4, reducing the gain of the signal representing noise sounds detected by the feedforward microphone 195 in response to a user of the communications headset 1000 speaking may be deemed desirable, as in the case of talk-through functionality, to avoid the conveyance of the user's own speech sounds to the user's own ears with an unnaturally high amplitude and/or with other unnaturally altered characteristics. Although it is commonplace for much of the range of frequencies of sound in which ANR is employed to be largely below the range of frequencies of sound normally associated with human speech, there is some degree of overlap between these two ranges. As a result, the speech sounds of a user of the communications headset 1000 (especially a user with a deeper voice) that are detected by the feedforward microphone 195 may be treated by the ANR circuit 695 as unwanted environmental noise sounds for which it generates anti-noise sounds that are caused to be acoustically output by the acoustic driver 115. This acoustic output of anti-noise sounds meant to reduce lower frequency portions of their speech may produce undesirable acoustic artifacts that the user may find unpleasant or distracting. Reducing the gain of the signal representing noise sounds detected by the feedforward ANR microphone 195 as the user speaks preserves at least some degree of ANR functionality, while also reducing at least the amplitude of such speech-based anti-noise sounds.

It should be noted that although FIG. 4 depicts the talk-through microphone 185 and the feedforward ANR microphone 195 as being separate and distinct microphones, alternate embodiments are possible in which a shared microphone replaces both to provide a common sound detection input for both functions. This may be possible due to both the talk-through microphone 185 and the feedforward ANR microphone 195 being acoustically coupled to the external environment, and due to both preferably not being noise-canceling type microphones such that they are both indeed able to detect far-field sounds along with near-field sounds (unlike the communications microphone 125, which as previously discussed, is a noise-canceling type of microphone structured to detect near-field sounds while largely ignoring far-field sounds). This depends, at least partially, on whether one or more locations exist on the structure of the communications headset at which a single microphone may be positioned (so as to be acoustically coupled to the external environment surrounding the communications headset 1000 and its user's head) that will allow detection of external sounds in a manner that will be effective for both functions.

Figure 5:
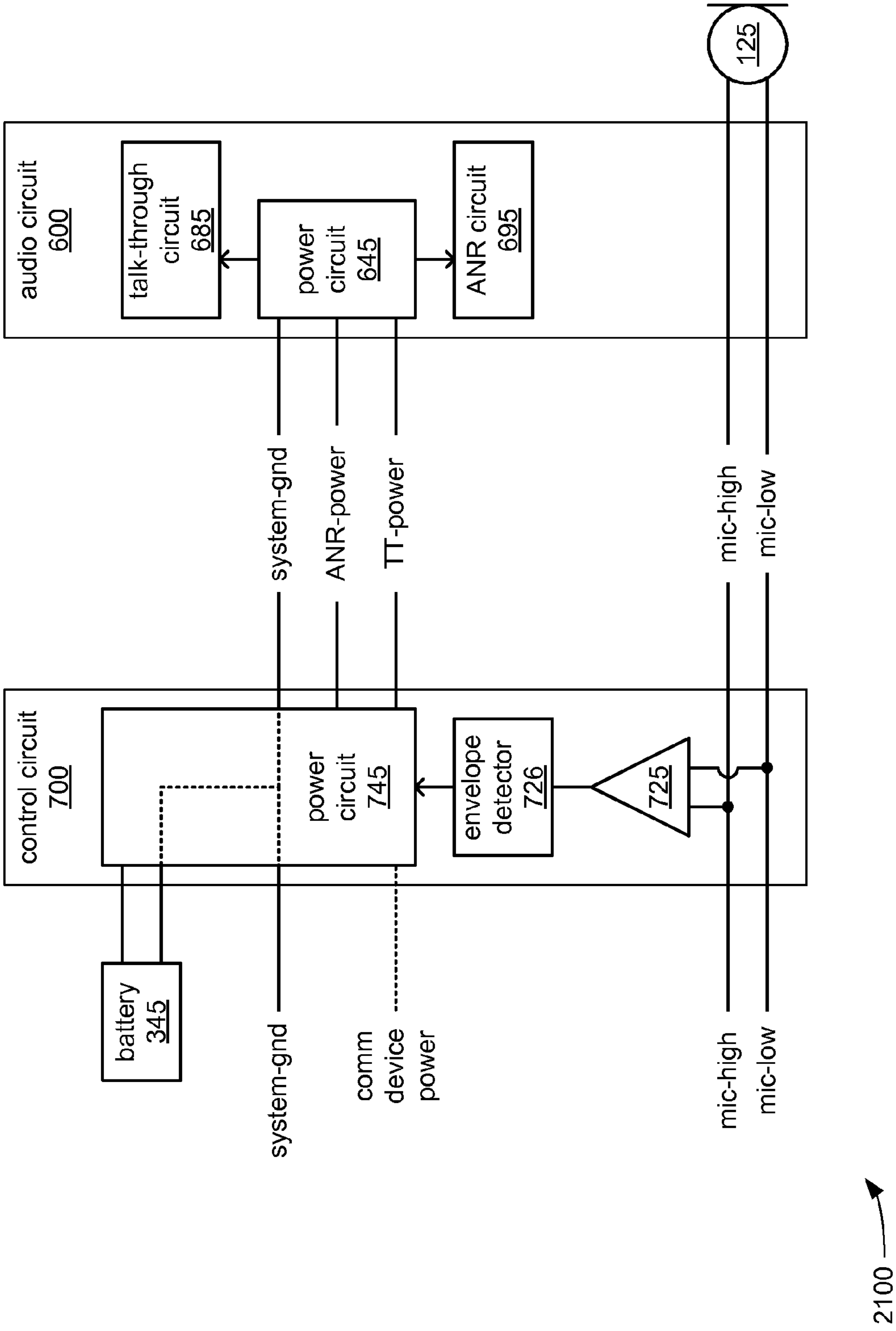
FIG. 5 is a block diagram of portions of still another variant of the electrical architecture of FIG. 2 incorporating at least variable talk-through gain.

FIG. 5 depicts portions of still another possible variant of the electrical architecture 2000 introduced in FIG. 2 germane to implementing automated variation in gain in the provision of talk-through functionality. Yet again, for sake of clarity, components of the audio circuit 600 associated with only one of the acoustic drivers 115 (e.g., the talk-through circuit 685 and the ANR circuit 695) are depicted, and thus, in embodiments having a pair of the earpieces 110, there would be a pair of the drivers 115, each of which would have a separate one of a pair of the talk-through circuits 685 and/or the ANR circuit 695 associated with it. This variant differs from the variant depicted in FIG. 4 only to the extent that components employed in detecting activity across mic-high and mic-low conductors for triggering a reduction in gain (for one or both of TT or ANR functionality) have been moved from the audio circuit 600 to the control circuit 700. Given the extensive treatment of numerous implementation details just provided with regard to FIGS. 3 and 4, it was deemed unnecessary to repeat the depiction of so much detail, and therefore, FIG. 5 presents a still higher-level view of a mechanism employed to alter gain(s) in response to instances of a user speaking.

More precisely, in this variant depicted in FIG. 5, the control circuit 700 incorporates a differential amplifier 725 and an envelope detector 726 (in place of the differential amplifier 625 and the envelope detector 626) to both detect activity across the mic-low and mic-high conductors, and integrate peaks in that activity to control the selective reduction of one or more gains in a manner not unlike what has been described in detail, above. However, given the more distant location of the differential amplifier 725 and the envelope detector 726 within the control box 300 from the location of the talk-through circuit 685 and the ANR circuit 695 within the head assembly (i.e., given the separation by the length of the upper cable 400), an additional signaling mechanism is interposed to convey signals to reduce gain(s) through the upper cable 400.

Yet more precisely, in this variant depicted in FIG. 5, the envelope detector 726 is coupled to the power circuit 745 of the control circuit 700, instead of more directly to components of one or both of the talk-through circuit 685 and the ANR circuit 695. Thus, it is the power circuit 745 that receives the resulting signal derived from the integration of signals from the communications microphone 125 that indicates when a gain should be reduced. In response to receiving an indication to reduce such a gain, the power circuit 745 alters a voltage level of the electrical power provided to one or both of the talk-through circuit 685 and the ANR circuit 695 through the upper cable 400. As depicted in this variant, in place of the earlier-depicted single head assembly power conductor, separate TT-power and ANR-power conductors are incorporated into the upper cable 400. The power circuit 745 is capable of separately varying the voltage level of the electrical power provided through one or the other of these cables.

For example, it may be that one of the manually-operable controls 335 is able to be employed by a user of the communications headset 1000 to cause the power circuit 745 to provide electric power to the talk-through circuit 685, or not. And further, while the power circuit 745 is so caused to provide such electrical power, one of the manually-operable controls 335 may be able to be employed by the user to select a gain to which a signal representing sounds detected by the talk-through microphone 185 is normally subjected. In response to such manual selection of that gain, the power circuit 745 signals the power circuit 645 concerning what the gain setting is to be by selecting a particular predetermined voltage level for the electrical power provided to the power circuit 645 via the TT-power conductor that is interpreted by the power circuit 645 as corresponding to that selected gain level, thereby causing the power circuit 645 to provide the appropriate signal to a gain input of the talk-through circuit 685 in place of the envelope detector 626 previously presented in the variants of FIGS. 3 and 4.

However, and continuing with this same example, where the power circuit 745 receives an indication from the envelope detector 726 to reduce gain, the power circuit 745 ceases to signal the power circuit 645 with the gain setting indicated manually by the user through manually-operable controls 335, and instead, selects a different predetermined voltage level with which to provide electrical power to the power circuit 645 (for use by the talk-through circuit 685) through the TT-power conductor. This different predetermined voltage level is interpreted by the power circuit 645 as indicating that this gain is to be set to a reduced gain level, and the power circuit 645 signals the talk-through circuit 685 through the same gain input to accordingly reduce this gain.

It should, again, be noted that although only a single acoustic driver 115 and its associated circuitry within the audio circuit 600 has been depicted in detail (especially in FIGS. 3 and 4) for the sake of clarity of discussion, this in no way should be taken to suggest that only embodiments having a single earpiece 110 with a single acoustic driver 115 and a single accompanying talk-through circuit 685 and/or a single accompanying ANR circuit 695 are possible. Embodiments of the communications headset 1000 are indeed contemplated that have a pair of the earpieces 110, each of which has its own one of a pair of acoustic drivers 115, and in which the audio circuit 600 actually incorporates a pair of one or both of the talk-through circuit 685 and the ANR circuit 695, in which one each of the talk-through circuit 685 and/or one each of the ANR circuit 695 is associated with and coupled to one of the acoustic drivers 115. In such embodiments, outputs of the envelope detector 626 are coupled to gain control inputs on each one a pair of the talk-through circuit 685 and/or each one of a pair of the ANR circuit 695—such that if both a pair of the talk-through circuit 685 and a pair of the ANR circuit 695 are present, then the single envelope detector 626 would output the results of its integration of peaks occurring in the signal representing sounds detected by the single communications microphone 125 to all four of these circuits 685 and 695.

It should be noted that although a single system-gnd conductor extending between the audio circuit 600 and the control circuit 700 has been depicted and discussed herein as being employed as the return path for both the provision of electric power and the provision of left and right audio channels to the acoustic drivers 115, other electrical architectures are envisioned in which separate ground conductors are employed as the return path for the provision of power and as the return path for the provision of left and right audio signals to the acoustic drivers 115. Although at least in the aviation field, it is common practice for an ICS to employ a single common ground conductor for these two functions, and therefore, it is likely that the lower cable 400 would convey a single common ground conductor from the communications device 9000 to the control box 300 (at least where the communications device 9000 is an ICS of an airplane), in alternate electrical architectures, separate ground conductors for these two functions may be provided within the upper cable 200 in which they are coupled to each other only at the location of the control circuit 700, and maintained as separate within the audio circuit 600. Indeed, it may be that such separation in ground conductors may be extended through the lower cable 400 such that they are coupled to each other only at the location of the connector(s) 490.

Other embodiments and implementations are within the scope of the following claims and other claims to which the applicant may be entitled.

The invention claimed is:

1. A communications headset comprising:

a first earpiece comprising:

a first casing; and a first acoustic driver disposed therein;

a first talk-through microphone carried by structure of the communications headset and acoustically coupled to an environment external to the communications headset;

an audio circuit coupled to the first acoustic driver and the first talk-through microphone, the audio circuit comprising a first talk-through circuit receiving a signal representing sounds detected by the first talk-through microphone and providing its output to the first acoustic driver;

a communications microphone positioned relative to the first casing of the earpiece towards the vicinity of a mouth of a user of the communications headset, wherein the communications microphone is noise-canceling microphone, wherein a gain of the signal representing sounds detected by the first talk-through microphone is reduced by a component of the first talk-through circuit in response to an instance of speech by a user of the communications headset being detected by the communications microphone, the first talk-through circuit comprising:

a first audio amplifier to drive the acoustic driver with the output of the first talk-through circuit;

a first envelope detector coupled to the output of the first audio amplifier to integrate peaks in a signal output by the first audio amplifier in driving the acoustic driver;

a first controllable attenuator interposed between the first talk-through microphone and an input of the first audio amplifier; and the first envelope detector and the first controllable attenuator cooperate to form a first closed-loop compressor to limit an amplitude of the signal output by the first audio amplifier in response to the signal output by the first audio amplifier exceeding a predetermined threshold.

2. The communications headset of claim 1, wherein:

the audio circuit further comprises a first ANR circuit receiving a signal representing noise sounds detected in the environment external to the communications headset, deriving anti-noise sounds, and providing the anti-noise sounds to the first acoustic driver; and a gain of the signal representing noise sounds is reduced by a component of the first ANR circuit in response to an instance of speech by a user of the communications headset being detected by the communications microphone.

3. The communications headset of claim 2, wherein the noise sounds are detected by the first talk-through microphone.

4. The communications headset of claim 2, further comprising a first ANR microphone coupled to the audio circuit, and wherein the noise sounds are detected by the first ANR microphone.

5. The communications headset of claim 1, further comprising:

a second earpiece comprising:

a second casing; and a second acoustic driver disposed therein;

a second talk-through microphone carried by structure of the communications headset and acoustically coupled to an environment external to the communications headset; and wherein:

the audio circuit is further coupled to the second acoustic driver and the second talk-through microphone;

the audio circuit further comprises a second talk-through circuit receiving a signal representing sounds detected by the second talk-through microphone and providing its output to the second acoustic driver; and a gain of the signal representing sounds detected by the second talk-through microphone is reduced by a component of the second talk-through circuit in response to an instance of speech by a user of the communications headset being detected by the communications microphone.

6. The communications headset of claim 1, wherein the first controllable attenuator comprises a voltage-controlled attenuator, and the audio circuit further comprises:

an amplifier coupled to the communications microphone; and wherein the first envelope detector is coupled to an output of the amplifier and coupled to a gain control input of the first controllable attenuator; and the first controllable attenuator is the component of the first talk-through circuit reducing the gain of the signal representing sounds detected by the first talk-through microphone.

7. A method of controlling sounds acoustically output by an acoustic driver of a communications headset to an ear of a user of the communications headset, comprising:

detecting speech sounds of a user of the communications headset using a noise-canceling communications microphone of the communications headset;

integrating peaks of a signal output by the communications microphone, wherein an envelope detector coupled to the communications microphone is employed to perform the integrating of the peaks;

reducing a gain of a signal representing sounds detected by a talk-through microphone of the communications headset in response to detecting the speech sounds of the user of the communications headset such that an amplitude of sounds detected by the talk-through microphone that are acoustically output by the acoustic driver is reduced; and controlling the reducing of the gain with the results of the integrating of the peaks, wherein a component of a talk-through circuit to which the talk-through microphone and the acoustic driver are coupled is employed to reduce the gain of the signal representing sounds detected by the talk-through microphone in a manner in which the combination of the envelope detector and the component of the talk-through circuit form an open-loop compressor.

8. The method of claim 7, wherein the component of the talk-through circuit is a voltage-controlled attenuator comprising a gain control input coupled to the envelope detector.

9. The method of claim 7, wherein the component of the talk-through circuit is an audio amplifier comprising a gain control input coupled to the envelope detector.

* * * * *